US012653857B2

(12) United States Patent (10) Patent No.: US 12,653,857 B2
Xie et al. (45) Date of Patent: Jun. 16, 2026

(54) ANESTHETIC METHOD OF SPOTTED SEABASS WITH PLANT ESSENTIAL OILS

(71) Applicant: Shanghai Ocean University, Shanghai (CN)

(72) Inventors: Jing Xie, Shanghai (CN); Jie Cao, Shanghai (CN); Jinfeng Wang, Shanghai (CN); Jun Mei, Shanghai (CN); Zhaoyang Ding, Shanghai (CN); Weiqiang Qiu, Shanghai (CN)

(73) Assignee: Shanghai Ocean University, Shanghai (CN)

( * ) Notice: Subject to any disclaimer, the term of this patent is extended or adjusted under 35 U.S.C. 154(b) by 265 days.

(21) Appl. No.: 18/679,405

(22) Filed: May 30, 2024

(65) Prior Publication Data

US 2024/0316136 A1 Sep. 26, 2024

(30) Foreign Application Priority Data

Mar. 26, 2024 (CN) .......................... 202410354967.3

(51) Int. Cl.
| | |
|---|---|
| *A61K 36/54* | (2006.01) |
| *A61K 9/107* | (2006.01) |
| *A61K 47/10* | (2017.01) |
| *A61K 47/26* | (2006.01) |
| *A61P 23/00* | (2006.01) |

(52) U.S. Cl.
CPC .............. *A61K 36/54* (2013.01); *A61K 9/107* (2013.01); *A61K 47/10* (2013.01); *A61K 47/26* (2013.01); *A61P 23/00* (2018.01)

(58) Field of Classification Search
None
See application file for complete search history.

(56) References Cited

FOREIGN PATENT DOCUMENTS

CN 113812357 B 9/2022

*Primary Examiner* — Michael V Meller

(57) ABSTRACT

An anesthetic method of the spotted seabass with a plant essential oil includes the following steps. (1) Spotted seabass is acclimated in a water tank for 24 h before anesthesia. The metabolic wastes of the spotted seabass were discharged during acclimatization period. (2) *Cinnamomum camphora* essential oil, ethanol, and Tween-80 are mixed and dissolved to obtain an emulsified essential oil. (3) The emulsified essential oil is respectively added into a plurality of aquariums. The spotted seabass is transferred into the plurality of aquariums. Concentrations of *Cinnamomum camphora* essential oils in the plurality of aquariums and anesthesia time of the spotted seabass are recorded. (4) The spotted seabass are captured and placed into an aquarium containing clean water for recovery when the spotted seabass enter the deep anesthesia period. The resuscitation time is recorded when the spotted seabass have no flopping, and swim normally and is active.

1 Claim, 20 Drawing Sheets

1

2

3

4

5

6

ANESTHETIC METHOD OF SPOTTED SEABASS WITH PLANT ESSENTIAL OILS

CROSS-REFERENCE TO RELATED APPLICATIONS

This application claims the benefit of priority from Chinese Patent Application No. 202410354967.3, filed on Mar. 26, 2024. The content of the aforementioned application, including any intervening amendments thereto, is incorporated herein by reference in its entirety.

TECHNICAL FIELD

This application relates to fish anesthesia, and more particularly to an anesthetic method of spotted seabass with plant essential oils.

BACKGROUND

Spotted seabass (*Lateolabrax maculatus*) belongs to osteichthyes, perciformes, species of bass, serranidae, *lateolabrax*, and is one of the main species of marine aquaculture fish. The spotted seabass has a significant edible and nutritional value as its flesh is tasty and rich in protein. However, due to the spotted seabass is easily stressed, its dorsal spines can easily injure each other during blood sampling, weighing and transportation, exacerbating the stress reaction of the live fish and leading to mortality, thus limiting the market scale of the spotted seabass.

Anesthesia is required for many procedures in commercial fisheries and aquaculture, including sorting, vaccinations, blood sampling, weighting and transportation to reduce stress and physical injuries to fish, thereby improving animal welfare. Fish anesthetics are categorized into two categories: synthetic and natural (derived from plants). The most commonly used synthetic anesthetics are tricaine methanesulphonate (MS-222, molecular formula $C_{10}H_{15}NO_5S$), benzocaine, quinaldine and 2-phenoxyethanol. Nevertheless, some synthetic anesthetics have been revealed to be expensive, stressful or have adverse side effects, such as excessive mucus production, gill irritation, suppression of the immune system and increased muscle tension. Nowadays, essential oils are studied as fish anesthetics and have emerged as suitable alternatives to synthetic anesthetics.

Plant-based anesthetics are increasingly being evaluated for their physiological, biochemical, and histopathological effects on fish. It is important to clarify the advantages and drawbacks of various plant-based anesthetics for each species, as this might have an impact on the health and well-being of fish. Anesthetics have the potential to significantly impact blood biochemical parameters such as blood cell counts, hematocrit value, glucose levels, hepatic enzymes, and immune status in fish. It has been reported an increase in plasma cortisol levels in meagre (*Argyrosomus regius*) exposed to Lippia alba essential oil. The glucose and cortisol levels in Nile tilapia (*Oreochromis niloticus*) treated to Alpinia galanga essential oil remained stable at normal levels, but the fish subjected to MS-222 exhibited elevated levels. In addition, the histopathological impacts of plant essential oils utilized as anesthetics on fish are of significant importance. The most severely affected organs in anesthesia studies are gills. According to Balamurugan et al., exposure to clove oil can lead to the buildup of extract on the gill tissues of clownfish. Jia et al. reported that they discovered histological alterations in the gills of spotted knifejaw (*Oplegnathus punctatus*) following exposure to clove oil.

The *Cinnamomum camphora*, a member of the Lauraceae family, is of significant biological value, which is utilised globally for medicinal, industry and spice applications over the world. The *Cinnamomum camphora* essential oil is isolated from branches and leaves of *Cinnamomum camphora* and has antioxidant, antibacterial and sedative properties. However, the application of *Cinnamomum camphora* essential oil in anesthesia of marine fish and its effects on their organism functions and stress responses have not been reported.

SUMMARY

This application provides an anesthetic method of spotted seabass with a plant essential oil and determines the feasibility of using *Cinnamomum camphora* essential oil, which is a natural plant extract, as a novel anesthetic for live fish, so as to slow down the stress response and tissue injury during transportation of live fish. This application further determines the blood biochemical stress levels, antioxidant enzyme activities and immune indexes, and explores the physiology and biochemistry, oxidative stress and gill tissue morphology of the spotted seabass anesthetized with *Cinnamomum camphora* essential oil, so as to provide a theoretical basis for the anesthesia treatment of marine fish.

Technical solutions of this application are described as follows.

This application provides an anesthetic method of spotted seabass with a plant essential oil, comprising:

(1) Spotted seabass temporary rearing: the spotted seabass are acclimated in a water tank for 24 h before anesthesia. The water quality parameters are maintained within following ranges: dissolved oxygen at 6.0 mg/L, temperature at 22±1° C., salinity of 16%, and pH at 7.5-8.0. Metabolic wastes of the spotted seabass are discharged during an acclimatization period;

(2) Emulsification of *Cinnamomum camphora* essential oil: emulsifying and dissolving *Cinnamomum camphora* essential oil, ethanol, and Tween-80 (polysorbate 80) to obtain an emulsified *Cinnamomum camphora* essential oil;

(3) Anesthesia: the emulsified *Cinnamomum camphora* essential oil are added into 7 aquariums at concentrations of 10, 20, 30, 50, 100, 150, and 200 mg/L, respectively. Then the spotted seabass are transferred to the 7 aquariums with the emulsified *Cinnamomum camphora* essential oils of different concentrations, respectively; the concentrations of *cinnamomum camphora* essential oils in the aquariums and anesthesia time of the spotted seabass are recorded.

(4) Recovery: the spotted seabass are extracted once deep anesthesia is achieved. Recovery is defined as the restoration of fish to their typical swimming behavior; and the resuscitation time of the spotted seabass is recorded.

In an embodiment, when the spotted seabass reach the deep anesthesia, the concentration of the *Cinnamomum camphora* essential oil is 150 mg/L.

In an embodiment, the step of "emulsification of *Cinnamomum camphora* essential oil" comprises the following steps:

(a) 10 mL of the *Cinnamomum camphora* essential oil, 200 mL of 50% ethanol and 1 mL of the Tween-80 are mixed in a volume ratio of 10:200:1, followed by slowly adding to 500 mL of water to form a mixture.

(b) The mixture is stirred by a magnetic stirrer followed by evaporating the mixture to obtain 100 mL of a concentrated solution.

In an embodiment, an evaporation temperature is 20-40° C.

In an embodiment, an emulsification temperature of the *Cinnamomum camphora* essential oil is 25° C.

In an embodiment, pH of 7.5.

In an embodiment, the spotted seabass has a weight of 500±25 g, a body length of 30±1 cm, and a respiration rate of 60-65 times/min measured by the number of times the gill cover of the spotted seabass is opened and closed within 1 min.

In an embodiment, the *Cinnamomum camphora* essential oil is purchased from Jiangxi Xuesong Natural Medicinal Oil Co., Ltd (China); and Tween-80 is purchased from Shanghai Anpu experiment Technology Co., Ltd.

This application has the following beneficial effects.

The essential oil anesthesia method provided herein can effectively reduce the tissue injury and stress response of the spotted seabass during the anesthesia process. Compared with the expensive MS-222 and linalool, the price of *Cinnamomum camphora* essential oil is only 1/10 thereof, which effectively reduces the anesthesia cost, and is particularly suitable for the vaccination, blood sampling, weighing and transportation of the live fish to obtain a higher economic benefit.

During the anesthesia of the spotted seabass, the *Cinnamomum camphora* essential oil can reduce the oxidative stress and metabolic disorder of the spotted seabass during the anesthesia process, relieves the anesthesia-induced damage to the gills, slow down the rise of the blood glucose and lactic acid of the spotted seabass, and will not inhibit the activities of alkaline phosphatase, immunoglobulin M and lysozyme of the spotted seabass, so as to maintain the immune function of the spotted seabass during the anesthesia.

DETAILED DESCRIPTION OF EMBODIMENTS

Figure 1A:
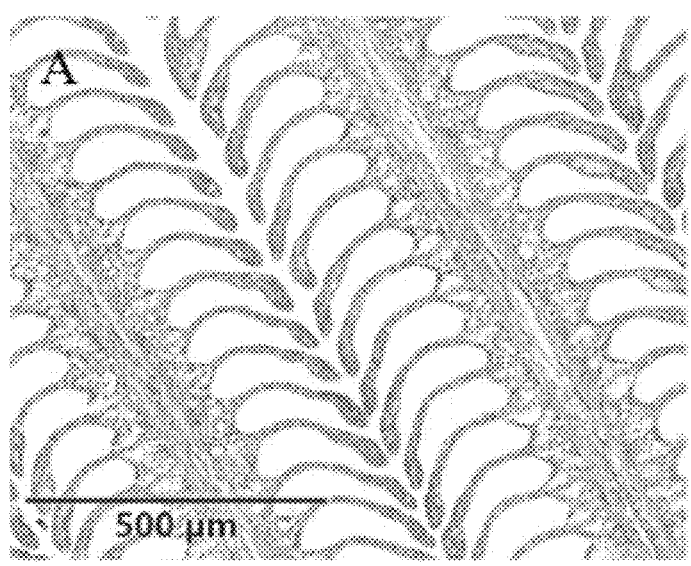
FIGS. 1A-1C are histopathological photos of gill tissues of the spotted seabass anesthetized with MS-222 according to an embodiment of the present disclosure; wherein A, gill tissue section of the spotted seabass before anesthesia; B, gill tissue section of spotted seabass after anesthesia by MS-222; C, gill tissue section of the spotted seabass anesthetized with MS-222 after 24 h of recovery; 1 shows chloride cell hyperplasia; 2 shows gill lamellar epithelium swelling; and 3 shows gill lamellar epithelium hyperplasia.

The technical solutions in the embodiments of the present disclosure will be clearly and completely described below. The present disclosure will be further described below in conjunction with the specific embodiments. For those skilled in the art, other embodiments obtained based on these embodiments without paying creative efforts should fall within the scope of the disclosure.

The *Cinnamomum camphora* essential oil in the disclosure was purchased from Jiangxi Xuesong Natural Medicinal Oil Co., Ltd (China) (RMB 139/500 mL); linalool was purchased from Aladdin Reagent (Shanghai) Co., Ltd (RMB 205.9/1 mL); MS-222 was purchased from Merck Bioscience & Technology GmbH (Germany) (RMB 810.23/10 g.), and MS-222 was a chemically synthesized anesthetic agent with the chemical name: tricaine methanesulfonate, molecular formula: $C_{10}H_{15}NO_5S$, used as an anesthetic for transportion of live fish; and Tween-80 was purchased from Shanghai Anpu experiment Technology Co., Ltd.

Composition Detection of Essential Oil

Chemical properties of the *Cinnamomum camphora* essential oil were analyzed by Gas Chromatography-Mass Spectrometer (GC-MS).

The essential oil samples were subjected to gas chromatography-mass spectrometry (GC-MS) analysis using Agilent® GC-7890 (America) fitted with Flame Ionization Detector (FID) detector. GC/MS analysis was performed under the subsequent parameters: capillary column, Agilent J&W HP-5 (30 m×0.25 mm; film thickness=0.25 m); inlet temperature: 140° C.; split ratio: 60:1; heater: 280° C.; chromatography conditions: Initial temperature 40° C., maintain for 5 min, 10° C./min to 250° C., then 5° C./min to 280° C., maintain for 5 min; extraction conditions: take 30 mL samples, add 30 mL ethyl acetate, take the supernatant after extraction, repeat the operation 3 times. 2 mL of the supernatant was precisely measured and stored in a glass centrifuge tube, concentrated in nitrogen at 40° C. in a water bath to nearly dry, dissolved in ethyl acetate, filtered with microporous filter membrane for GC-MS/MS detection, and the composition of the resulting *Cinnamomum camphora* essential oil was shown in Table 1.

TABLE 1

The composition of the Cinnamomum camphora essential oil

| Essential oil | Name | Retention time | Weight (%) |
|---|---|---|---|
| Cinnamomum camphora essential oil | 1,6-Octadien-3-ol,3,7-dimethyl | 16.949 | 73.70 |
| | Bicyclo[2.2.1]heptan-2-ol,1,7,7-trimethyl-, (1S-endo)- | 18.634 | 3.91 |
| | Geraniol | 21.270 | 3.17 |
| | 2,6-Octadien-1-ol,3,7-dimethyl-, (Z)- | 20.512 | 2.23 |
| | .alpha.-Terpineol | 19.391 | 1.92 |
| | Selina-6-en-4-ol | 28.840 | 1.58 |
| | Caryophylleneoxide | 28.332 | 1.14 |
| | Other | — | 12.35 |

As shown in Table 1, linalool (1,6-Octadien-3-ol,3,7-dimethyl) (73.70%) was the main component in the *Cinnamomum camphora* essential oil. Studies had shown that linalool has anesthetic and sedative effects on fish. However, linalool is expensive in the market (1 mL, 205.9 RMB, Aladdin Reagent Co., Ltd.). Moreover, due to the heat sensitivity, it is difficult to isolate and purify linalool from essential oils, and the purified product is prone to contain other impurities. Therefore, economic and safe plant essential oils are often used for fish anesthesia, such as basil essential oil (containing 53.35% linalool), lavender essential oil and coriander essential oil. The *Cinnamomum camphora* essential oil used in the disclosure has more than 70% linalool and has good potential as a fishing anesthetic.

Example 1

1. Preparation Method 1 of Essential Oil Emulsion 200 mL of 50% ethanol, 1 mL of Tween-80, and 10 mL of the *Cinnamomum camphora* essential oil were mixed, slowly added dropwise to 500 mL of water, magnetically stirred for 100 min at 15° C., and then concentrated to 100 mL by a rotary evaporator. The concentration of the *Cinnamomum camphora* essential oil in the emulsion was calculated by heating and distillation. The obtained concentration of *Cinnamomum camphora* essential oil was shown in Table 2.

2. Preparation Method 2 of Essential Oil Emulsion 200 mL of 50% ethanol, 1 mL of Tween-80, and 10 mL of the *Cinnamomum camphora* essential oil were mixed, slowly added dropwise to 500 mL of water, magnetically stirred for 100 min at 20° C., and then concentrated to 100 mL by a rotary evaporator. The concentration of the *Cinnamomum camphora* essential oil in the emulsion was calculated by heating and distillation. The obtained concentration of *Cinnamomum camphora* essential oil was shown in Table 2.

3. Preparation Method 3 of Essential Oil Emulsion 200 mL of 50% ethanol, 1 mL of Tween-80, and 10 mL of the *Cinnamomum camphora* essential oil were mixed, slowly added dropwise to 500 mL of water, magnetically stirred for 100 min at 25° C., and then concentrated to 100 mL by a rotary evaporator. The concentration of the *Cinnamomum camphora* essential oil in the emulsion was calculated by heating and distillation. The obtained concentration of *Cinnamomum camphora* essential oil was shown in Table 2.

4. Preparation Method 4 of Essential Oil Emulsion 200 mL of 50% ethanol, 1 mL of Tween-80, and 10 mL of the *Cinnamomum camphora* essential oil were mixed, slowly added dropwise to 500 mL of water, magnetically stirred for 100 min at 30° C., and then concentrated to 100 mL by a rotary evaporator. The concentration of the *Cinnamomum camphora* essential oil in the emulsion was calculated by heating and distillation. The obtained concentration of *Cinnamomum camphora* essential oil was shown in Table 2.

5. Preparation Method 5 of Essential Oil Emulsion 200 mL of 50% ethanol, 1 mL of Tween-80, and 10 mL of the *Cinnamomum camphora* essential oil were mixed, slowly added dropwise to 500 mL of water, magnetically stirred for 100 min at 40° C., and then concentrated to 100 mL by a rotary evaporator. The concentration of the *Cinnamomum camphora* essential oil in the emulsion was calculated by heating and distillation. The obtained concentration of *Cinnamomum camphora* essential oil was shown in Table 2.

6. Preparation Method 6 of Essential Oil Emulsion 200 mL of 50% ethanol, 1 mL of Tween-80, and 10 mL of the *Cinnamomum camphora* essential oil were mixed, slowly added dropwise to 500 mL of water, magnetically stirred for 100 min at 45° C., and then concentrated to 100 mL by a rotary evaporator. The concentration of the *Cinnamomum camphora* essential oil in the emulsion was calculated by heating and distillation. The obtained concentration of *Cinnamomum camphora* essential oil was shown in Table 2.

TABLE 2

The concentration of the Cinnamomum camphora essential oil under different evaporation temperatures

| No. | Evaporation temperature | Concentration of the Cinnamomum camphora essential oil (g/100 mL) |
|---|---|---|
| 1 | 15 | Incomplete emulsification |
| 2 | 20 | 9.7 |
| 3 | 25 | 9.8 |
| 4 | 30 | 9.6 |
| 5 | 40 | 9.4 |
| 6 | 45 | 8.5 |

As shown in Table 2, the emulsification temperature of the *Cinnamomum camphora* essential oil should be controlled to 20-40° C. The concentration of the *Cinnamomum camphora* essential oil obtained at 25° C. was the highest. When the temperature was lower than 20° C., the emulsifier (Tween-80) had a low solubility, and the emulsification was incomplete. When the temperature was higher than 40° C., the *Cinnamomum camphora* essential oil was volatile.

Example 2

1. Healthy spotted seabass with uniform sizes and uniform respiration rates were selected and acclimated for 24 h. During the acclimatization period, the water temperature was 22±1° C., the salinity was 16%, the dissolved oxygen was 6 mg/L, pH was 7.5, and the fish-water ratio was 1:50. The metabolic wastes of the spotted seabass were discharged during acclimatization period.

2. The emulsified *Cinnamomum camphora* essential oils were added to the aquariums respectively. The water temperature was controlled at 22±1° C. The concentrations of the emulsified *Cinnamomum camphora* essential oil were 10, 20, 30, 50, 100, 150, 200 mg/L, respectively, and the same concentrations of MS-222 anesthesia solution and linalool solution were prepared at the same time.

3. The spotted seabass were transferred to aquariums (5 fish per aquarium) with different concentrations of the *Cinnamomum camphora* essential oil, MS-222 and linalool anesthetics, and anesthetic concentrations, sedation concentrations and duration of anesthesia were recorded for the spotted seabass.

4. The fish were extracted once deep anesthesia was achieved. Recovery was defined as the restoration of fish to their typical swimming behavior; the resuscitation time of the spotted seabass were recorded.

5. The optimal concentration range was obtained, and oxidative stress and tissue injury were measured.

TABLE 3

Sedation, anesthesia and recovery stages of fish

| Stage | Description | Behavior exhibited |
|-------|-------------|--------------------|
| I | Light sedation | Equilibrium normal, slow swimming, decreased reactivity to external stimuli, slight decrease in opercular rate |
| II | Deep sedation | Restlessness, equilibrium normal, voluntary swimming still possible; slight decrease in opercular rate no respond to weak external stimulus |
| III | Light anesthesia | Partial loss of equilibrium; swimming erratic; increased opercular rate; reactive only to strong tactile and vibrational stimuli |
| IV | Deep anesthesia | Total loss equilibrium, lying on one side without movement, opercular movements slow and irregular; loss of all reflexes |
| | Recovery | Regaining of equilibrium and active swimming |

In accordance with the principles and guiding regulations established by the Animal Protection and Utilization Committee of Shanghai Ocean University (SHOU-DW-2022-059), 200 mg/L MS-222 was used to anesthetize fish. Venous-arterial blood samples were obtained from the caudal vein using a 1 mL syringe with 10% EDTA as an anticoagulant and then preserved in anticoagulation tubes. In addition, another portion of the blood was collected without anticoagulant, then kept at 4° C. for a duration of 12 hours for stationary. The coagulated blood was centrifuged at 4000×g for 20 min at 4° C. The serum was extracted and placed in the refrigerator at −40° C. for testing.

7. Determination of Indicators 7.1 Observation by Light Microscope

Gill tissues were collected for histological observation. Tissues were fixed using a 4% paraformaldehyde solution and dehydrated in gradient ethanol, permeated with xylene and then placed within paraffin for embedding. Sections (5 m) were prepared. Hematoxylin and eosin were then used to stain the samples for examination. Observation was performed under a light microscope (Olympus BX-43, Japan).

7.2 Blood Biochemical Analysis

Red blood cell count (RBC), haematocrit (HCT), and hemoglobin (HGB) in blood samples were measured in a Myriad Veterinary Automatic Blood Cell Analyser (BC-2800vet, Shenzhen, China).

7.3 Measurement of Energy Metabolism Indexes

Acid phosphatase (ACP), glucose (GLU) and lactic acid (LD) kits (Nanjing Jiancheng Bioengineering Institute, Nanjing, China) were used to measure ACP, GLU and LD levels.

7.4 Determination of Oxidative Stress Indicators

Superoxide Dismutase (SOD), Catalase (CAT) and Glutathione Peroxidase (GSH-Px) kits (Nanjing Jiancheng Bioengineering Institute, Nanjing, China) were used to determine SOD, CAT and GSH-Px activities in blood.

7.5 Determination of Immunological Indicators

Lysozyme (LZM) activity was determined by the method of De Souza et al. Serum immunoglobulin M (IgM) concentration was measured using a fish ELISA kit (Nanjing Jiancheng Bioengineering Institute, Nanjing, China).

7.6 Data Analysis

One-way analysis of variance (ANOVA) was used to evaluate the data (anesthetic induction and recovery time) using SPSS 26.0 software (SPSS Inc., Chicago, IL, USA). The significant variation was determined using Duncan's multiple range test ($P<0.05$). Graphs were created using Origin software.

Example Results and Analyses

1. Sedation Concentration, Anesthesia Induction Concentration and Resuscitation Time of Different Essential Oils As shown in Table 4, the anesthesia induction time of the spotted seabass anesthetized with MS-222, *Cinnamomum camphora* essential oil and linalool decreased with increase of concentration. MS-222, *Cinnamomum camphora* essential oil and linalool all showed a light sedation effect (Stage I) at 10 mg/L concentration, deep sedation at 20 mg/L concentration. MS-222 and linalool showed light anesthesia effects at 30 mg/L concentration and *Cinnamomum camphora* essential oil at 50 mg/L concentration (Stage III). The minimum concentration of MS-222 required to achieve profound anesthesia (Stage IV) in fish was found to be 50 mg/L, 100 mg/L concentration *Cinnamomum camphora* essential oil and 50 mg/L concentration linalool, respectively. Recovery time of fish anesthetized with MS-222, *Cinnamomum camphora* essential oil and linalool increased with increasing concentration. An ideal anesthetic should achieve anesthesia induction in around 3 min and recovery within 5 min. In this investigation, it was found that the minimum concentration of *Cinnamomum camphora* essential oil needed to achieve deep anesthesia in spotted seabass was determined to be 150 mg/L based on this criterion. The anesthetic induction time in this concentration was 175.67 s, and recovery time was 220.33 s. The optimal anesthetic concentration of MS-222 for spotted seabass was 100 mg/L. Compared to *Cinnamomum camphora* essential oil, the spotted seabass took longer to resuscitate after deep anesthesia by MS-222. In this study, the optimal anesthetic concentration of linalool for spotted seabass was 100 mg/L. Spotted seabass were able to be anesthetised into the deep anesthesia (Stage IV) within 3 min (155.33 s) at this concentration. However, its resuscitation time was much longer than that of spotted seabass anesthetised by aramid oil and MS-222. However, its resuscitation time was over 5 min (344.00 s), much longer than that of spotted seabass anesthetised by *Cinnamomum camphora* essential oil and MS-222, suggesting that it was not an ideal anesthetic for fishing.

TABLE 4

Sedation, anesthesia stage and resuscitation time of spotted seabass
exposed to different concentrations of Cinnamomum camphora essential oil, MS-222
and linalool

| Anesthetics | Concentration (mg/L) | Stage I (s) | Stage II (s) | Stage III (s) | Stage IV (s) | Resuscitation time (s) |
|---|---|---|---|---|---|---|
| MS-222 | 5 | — | — | — | — | — |
| | 10 | 90.67 ± 2.08 | — | — | — | — |
| | 20 | 73.67 ± 5.86 | 111.67 ± 2.08 | — | — | — |
| | 30 | 59.00 ± 3.00 | 102.33 ± 2.52 | 122.67 ± 2.52 | — | — |
| | 50 | 39.67 ± 2.52 | 64.00 ± 3.61 | 83.00 ± 3.00 | 185.00 ± 4.36 | 217.00 ± 2.00 |
| | 100 | 30.00 ± 3.00 | 41.00 ± 4.58 | 70.67 ± 4.04 | 174.00 ± 4.58 | 240.00 ± 2.00 |
| | 150 | 20.67 ± 2.52 | 35.00 ± 2.00 | 63.00 ± 3.61 | 147.67 ± 2.52 | 290.33 ± 3.06 |
| | 200 | 19.67 ± 2.52 | 29.67 ± 2.52 | 55.33 ± 2.08 | 140.33 ± 2.08 | 349.33 ± 3.06 |
| Cinnamomum camphora | 5 | — | — | — | — | — |
| | 10 | 121.00 ± 3.61 | — | — | — | — |
| | 20 | 94.33 ± 4.04 | 151.67 ± 3.06 | — | — | — |
| | 30 | 76.67 ± 3.21 | 131.67 ± 4.51 | — | — | — |
| | 50 | 58.00 ± 4.58 | 107.33 ± 8.33 | 192.00 ± 3.00 | — | — |
| | 100 | 47.00 ± 2.65 | 81.00 ± 3.61 | 150.00 ± 3.00 | 211.00 ± 3.61 | 181.00 ± 3.61 |
| | 150 | 37.00 ± 5.00 | 48.67 ± 1.53 | 61.67 ± 5.51 | 175.00 ± 3.61 | 220.00 ± 4.58 |
| | 200 | 24.67 ± 1.53 | 39.00 ± 2.00 | 49.33 ± 2.08 | 126.33 ± 3.06 | 311.67 ± 1.53 |
| Linalool | 5 | — | — | — | — | — |
| | 10 | 88.67 ± 3.21 | — | — | — | — |
| | 20 | 70.00 ± 3.00 | 97.00 ± 4.58 | — | — | — |
| | 30 | 60.00 ± 3.00 | 84.67 ± 3.51 | 103.33 ± 3.51 | — | — |
| | 50 | 42.67 ± 3.51 | 75.33 ± 2.52 | 115.00 ± 4.00 | 323.33 ± 2.52 | 235.00 ± 2.00 |
| | 100 | 31.67 ± 1.15 | 75.00 ± 2.65 | 103.67 ± 2.52 | 213.00 ± 1.73 | 255.33 ± 2.08 |
| | 150 | 22.33 ± 2.52 | 44.00 ± 2.65 | 91.67 ± 1.53 | 155.33 ± 3.51 | 270.00 ± 3.00 |
| | 200 | 16.00 ± 1.00 | 37.00 ± 1.73 | 86.00 ± 2.65 | 141.00 ± 5.29 | 310.00 ± 3.00 |

Data were expressed as mean ± standard deviation. -: No anesthetic effect.

2. Changes in Tissue Damage

Figure 1B:
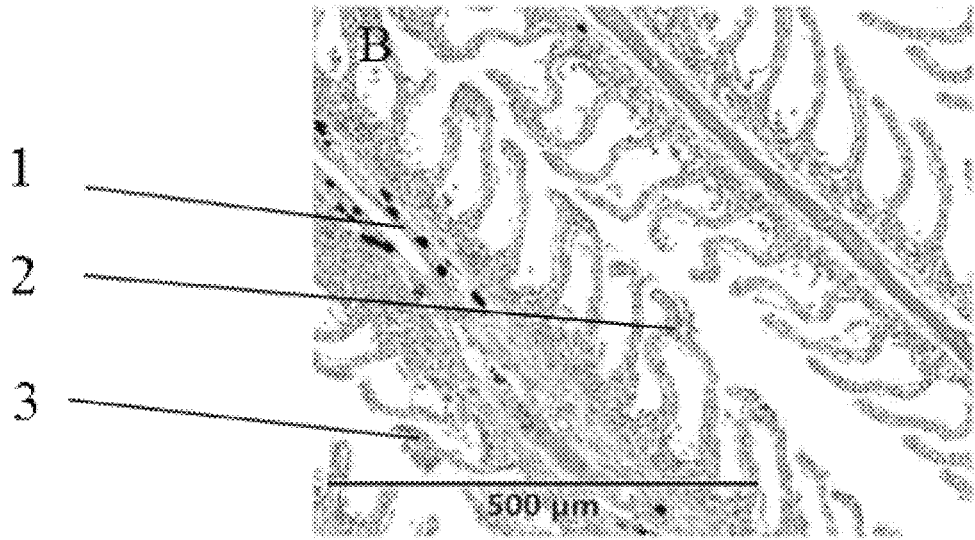
Figure 1C:
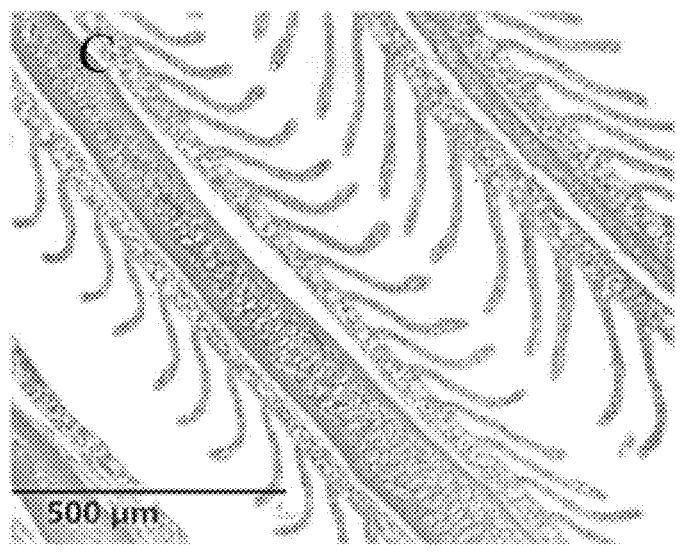
Figure 2A:
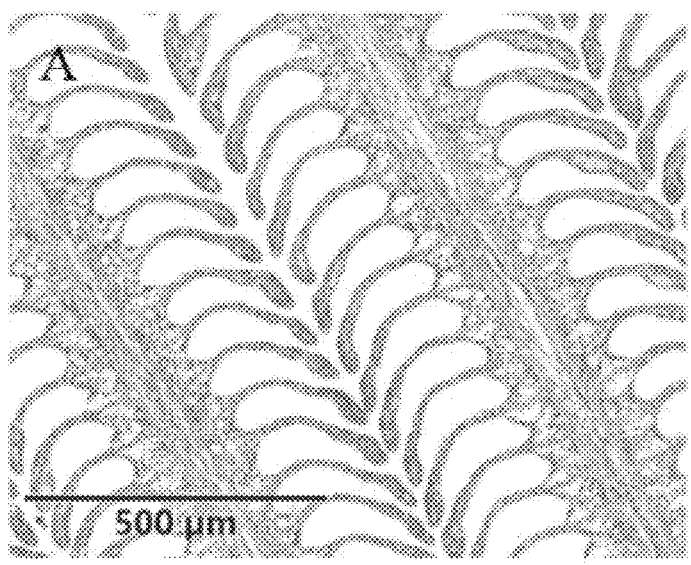
FIGS. 2A-2C are histopathological photos of gill tissues of spotted seabass anesthetized with the *Cinnamomum camphora* essential oil according to an embodiment of the present disclosure; wherein A, gill tissue section of the spotted seabass before anesthesia; B, gill tissue section of the spotted seabass after anesthesia by the *Cinnamomum camphora* essential oil; and C, gill tissue section of the spotted seabass anesthetized with the *Cinnamomum camphora* essential oil after 24 h of recovery.
Figure 2B:
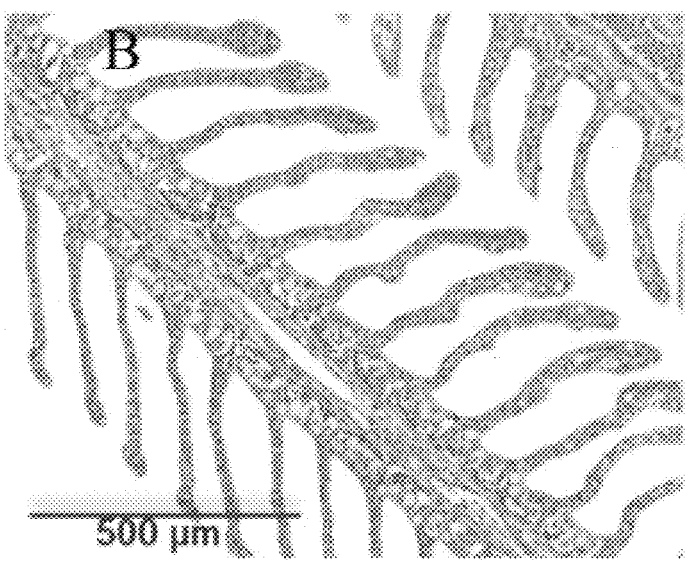
Figure 2C:
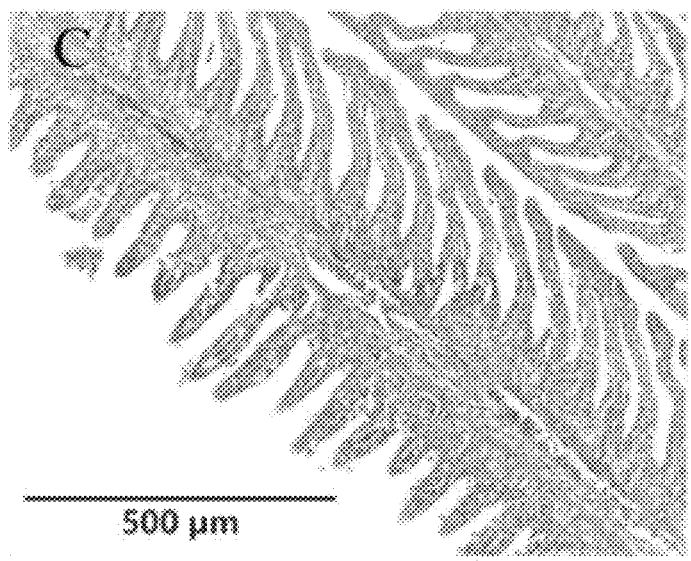
Figure 3A:
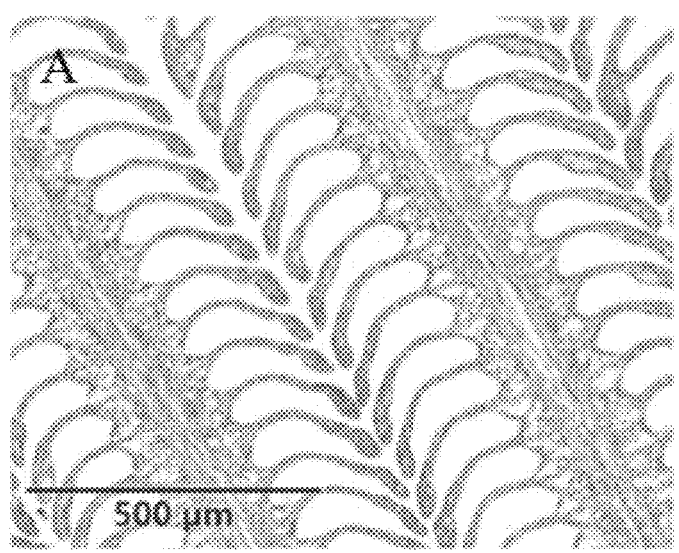
FIGS. 3A-3C are histopathological photos of gill tissue of the spotted seabass anesthetized with linalool according to an embodiment of the present disclosure; wherein A, gill tissue section of seabass before anesthesia; B, gill tissue section of the spotted seabass after anesthesia by linalool; C, gill tissue section of the spotted seabass anesthetized with linalool after 24 h of recovery; 4 shows gill lamellar epithalaxia; 5 shows gill lamellar epithelium swelling; and 6 shows gill lamellar epithalaxia.
Figure 3B:
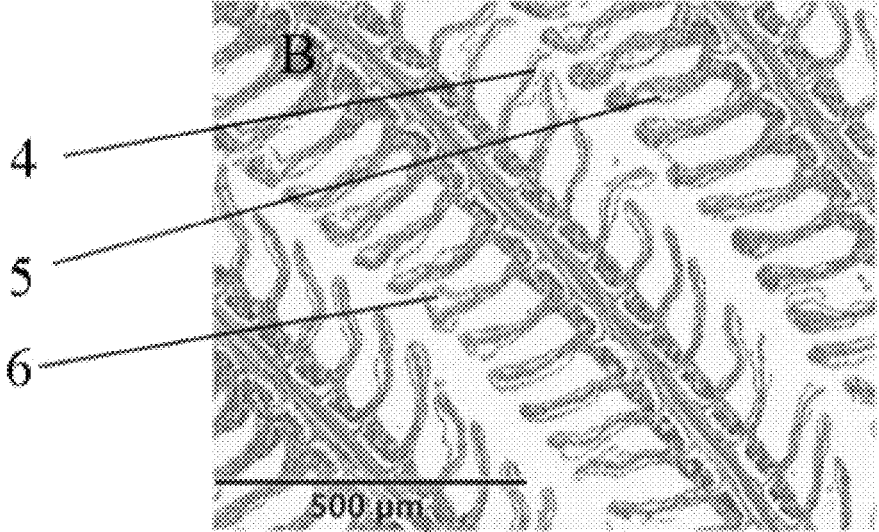
Figure 3C:
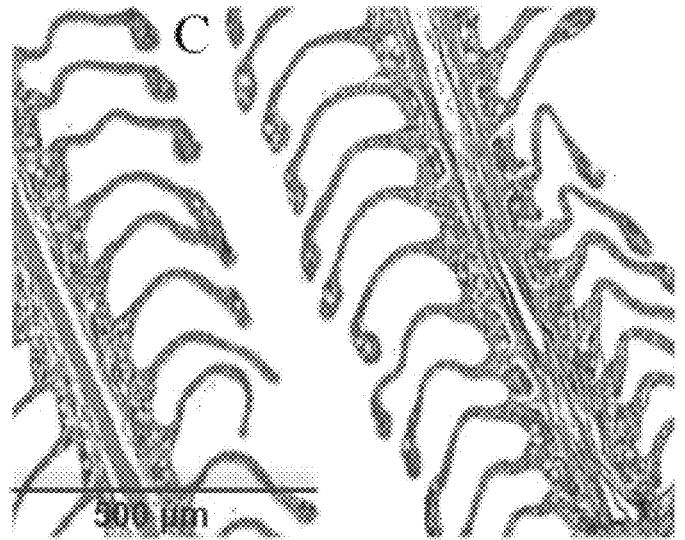

Histopathological investigations are essential for confirming the susceptibility of organs to toxic chemicals, particularly the gill epithelium, which is the primary location for gas exchange and osmoregulation. FIG. 1A represented a gill tissue section of spotted seabass before anesthesia. Referring to FIG. 1B, after anesthesia using MS-222, chloride cells underwent significant proliferation (1), gill tissue lamellar epithelium (2) swelled, and lamellar epithelium (3) underwent proliferation. As shown in FIGS. 2B and 2C, no significant changes were seen after using the Cinnamomum camphora essential oils. As shown in FIG. 3B, after anesthesia of the spotted seabass with linalool, the gill tissues of the fish appeared to swollen lamellar epithelium (5) and epithelial hyperplasia (4) and (6). FIG. 1A showed that the swelling of the gill lamellar epithelium of seabass anesthetized with MS-222 (2) was more severe, and chloride cell hyperplasia (1) and lamellar epithelium hyperplasia (3) also appeared. FIG. 3B showed the spotted seabass anesthetized with linalool appeared to have the gill lamellar epithalaxia in the positions (4) and (6), and the fish was subjected to stress during the anesthesia process, and gill tissues would have undergone changes to adapt to the new conditions. Morphological changes indicated that fish developed adaptive strategies to protect important physiological functions, including gas exchange, acid-base balance, osmotic pressure regulation, and excretion of nitrogenous compounds. Because gills were directly exposed to the aquatic environment, the gills were vulnerable to various injuries (traumatic, toxicological, and infectious), and fish tissues could only respond to unfavorable stimuli in a limited way. This also explained the presence of epithelial swelling and hyperplasia of the gill lamellar epithelium observed in gill tissue sections under anesthesia. After 24 h recovery, the histopathological changes of spotted seabass in each experimental group were recovered to varying degrees. This indicated that the gill tissue injury caused by three anesthetics to spotted seabass was reversible. This was a defense mechanism of fish to cope with external stress and was a reparable non-specific response. Compared to MS-222 and linalool, the spotted seabass anesthetized with the Cinnamomum camphora essential oil suffered less stress damage during anesthesia and recovery, as shown in FIG. 2C, indicating a higher degree of recovery after anesthesia.

3. Blood Biochemical Analysis

Figure 4A:
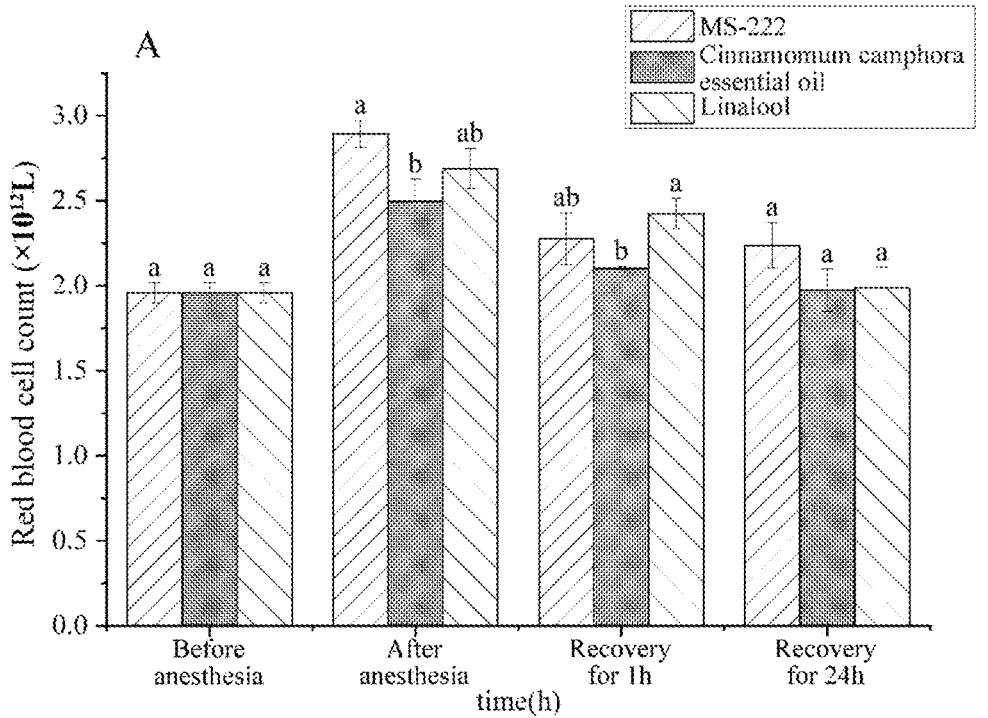
FIGS. 4A-4C show effects of MS-222, *Cinnamomum camphora* essential oil, and linalool anesthesia on hematological levels of the spotted seabass; wherein A, red blood count; B, hematocrit value; and C, hemoglobin.
Figure 4B:
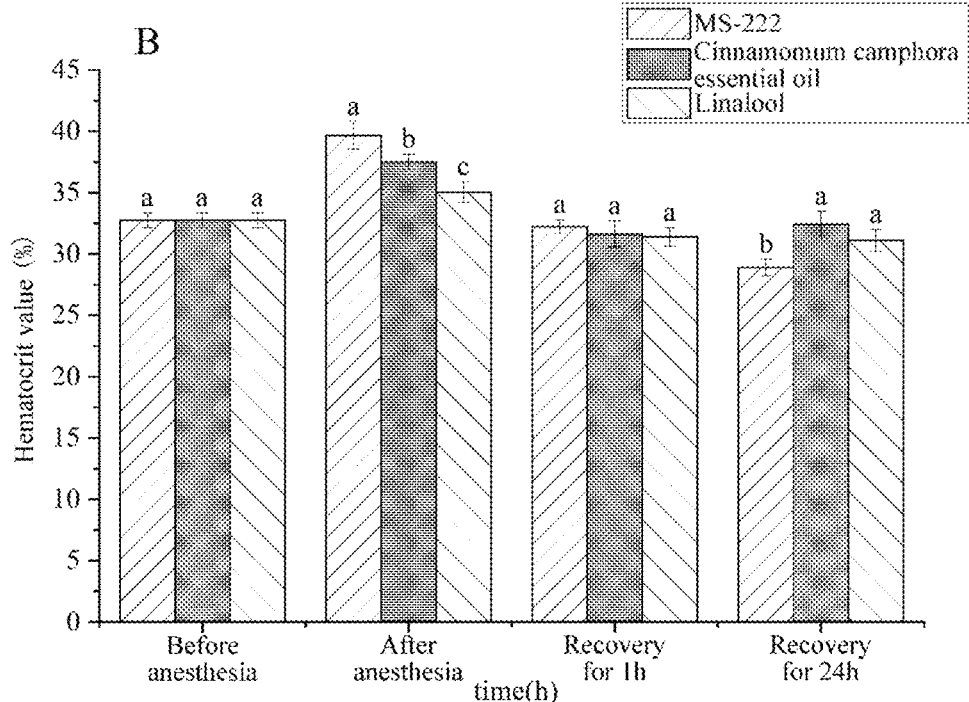
Figure 4C:
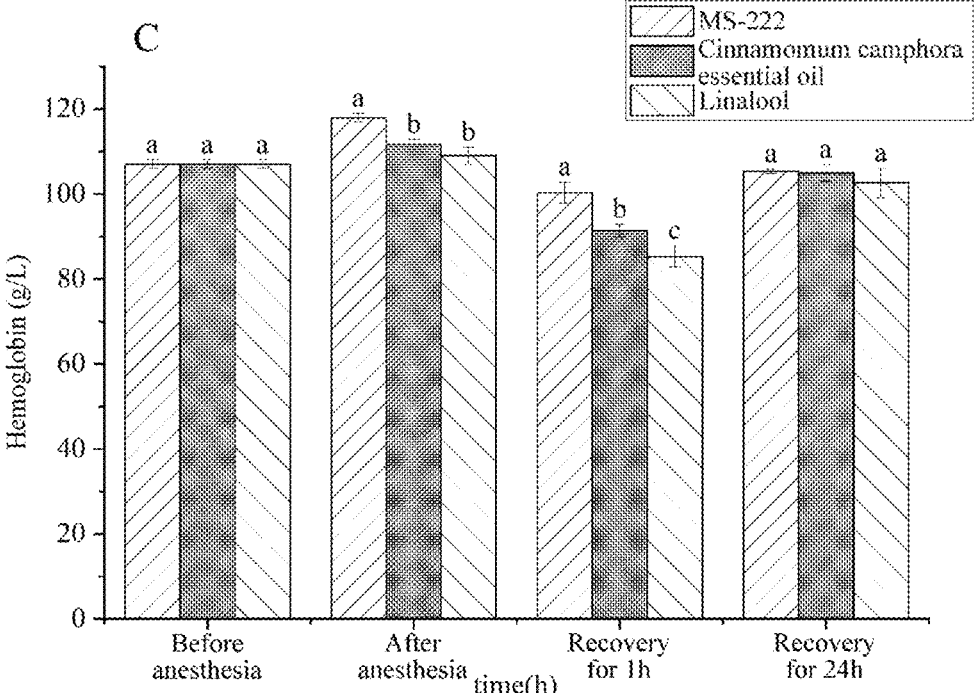

As shown in FIGS. 4A-4C, after being deeply anesthetised, spotted seabass showed an increase in red blood cell counts (RBC), hemoglobin concentration and hematocrit. In the comparison of different anesthetic treatments, the following trends were observed: the RBC, percentage of hematocrit and hemoglobin concentration were higher in fish from the MS-222 group than those in fish from the Cinnamomum camphora essential oil group (p<0.05). The percentage of hematocrit in fish from the linalool group was lower in than that in fish from MS-222 and Cinnamomum camphora essential oil groups (p<0.05). During recovery from anesthesia, the RBC, percentage of hematocrit and the hemoglobin concentration in spotted seabass decreased, gradually returned to initial levels. However, after 24 h of recovery, the spotted seabass anaesthetised with MS-222 showed higher RBC and lower percentage of hematocrit than initial values (p<0.05). Compared to Cinnamomum camphora essential oil, the higher number of RBC in spotted seabass anesthetized with MS-222 and linalool might be an increased requirement for oxygen transportation due to the rise in energy demand, which was prompted by the stress experienced by the fish when exposed to these solutions. Comparable outcomes were achieved for tambaqui that were anesthetized with clove oil. Nevertheless, when evaluating the essential oil O. gratissimum in juvenile matrinxã B. amazonicus, Ribeiro et al. noticed a drop in RBC after 24 hours. This discovery illustrates that the reactions of RBCs, which are linked to defensive competence, differ greatly among different species of fish, including those that are closely related. There was no significant difference in the percentage of hematocrit among each of the treatments following anesthesia, indicating that the concentration of anesthetic in *Cinnamomum camphora* essential oil did not have an impact on the hematological pattern. Comparable outcomes were noted in tambaqui anesthetized with clove oil and in juveniles of matrinxã *Brycon amazonicus* anesthetized with *Ocimum gratissimum* essential oil. Ventura et al. suggested that the increase in hematocrit when evaluating the effects of each treatment at various time points, it might be an adaptive reaction without physiological implications. The rise in hemoglobin levels in fish anesthetized with MS-222, *Cinnamomum camphora* essential oil and linalool and evaluated after deep anesthesia signified an enhanced ability of erythrocytes to carry oxygen. Researches have demonstrated that these changes occur as a result of the increased physiological requirements caused by an adverse circumstance. Thus, the observed changes in hematological alterations suggest that the *Cinnamomum camphora* essential oil was better effective in preventing stress than MS-222 during anesthesia. This needs adaptive response mechanisms from fish following anesthesia. Nevertheless, after 24 h, the hemoglobin levels had returned to a state of equilibrium.

4. Energy Metabolism

Figure 5A:
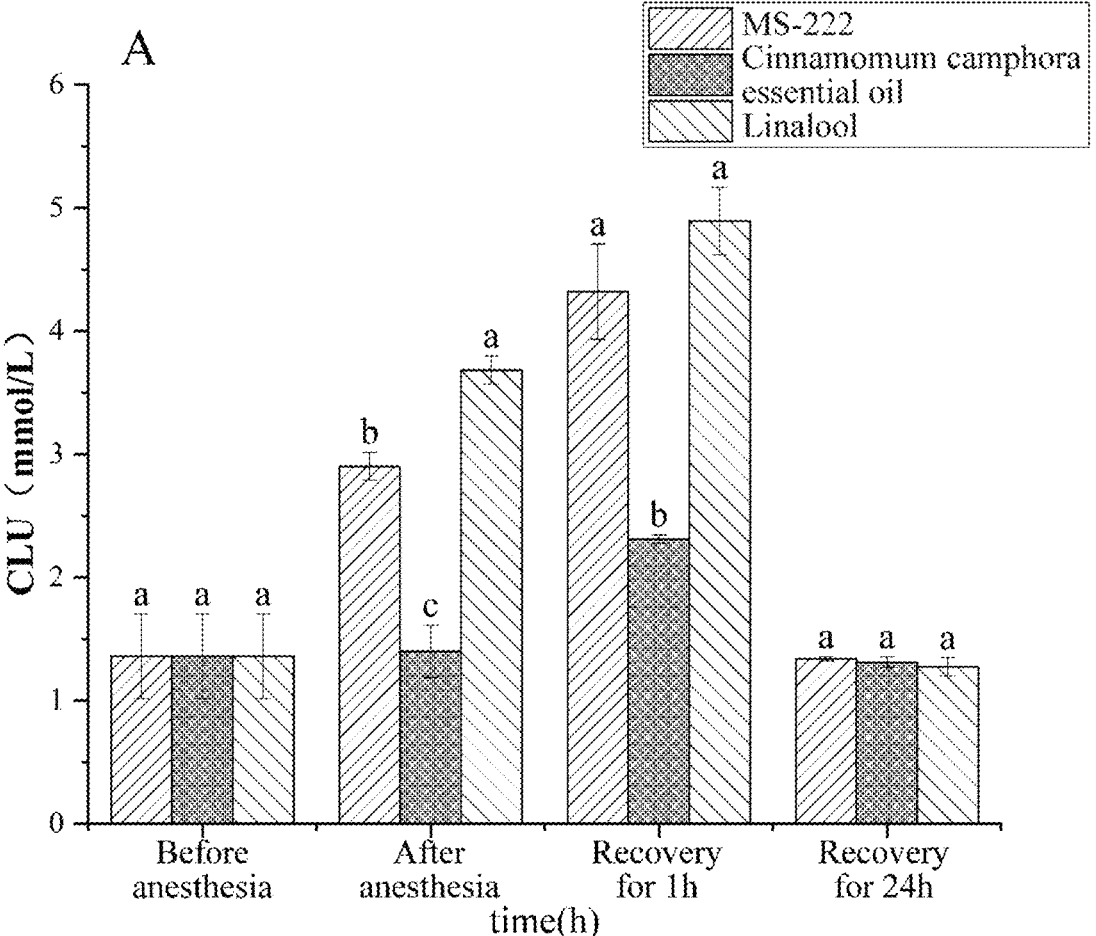
FIGS. 5A-5B show effects of MS-222, *Cinnamomum camphora* essential oil, and linalool anesthesia on energy metabolism of the spotted seabass; wherein A, glucose (GLU) content; and B, lactic acid (LD) content.
Figure 5B:
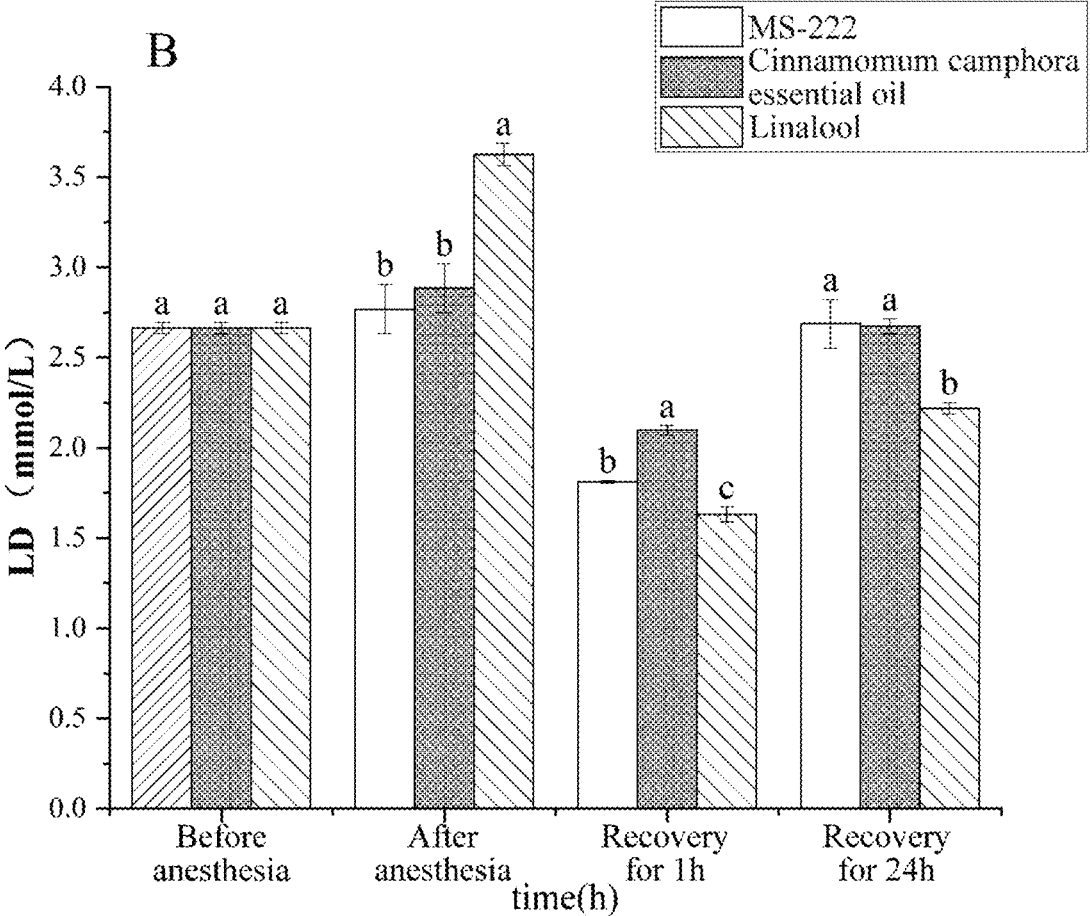

Greater concentrations of glucose were detected (P<0.05) in fish that were anesthetized with MS-222 and linalool than that in fish anesthetized with *Cinnamomum camphora* essential oil. Meanwhile, a greater level of lactic acid was observed (P<0.05) in fish anesthetized with linalool than that in fish anesthetized with MS-222 and *Cinnamomum camphora* essential oil. After 24 h of recovery, the glucose concentration was still higher (P<0.05) in fish anesthetized with linalool in comparison to that in fish anesthetized with MS-222 and *Cinnamomum camphora* essential oil (FIG. 5 A). However, the lactic acid concentration was lower (P<0.05) in fish anesthetized with linalool than that in fish anesthetized with MS-222 and *Cinnamomum camphora* essential oil (FIG. 5 B). When under stress, the fish activate the hypothalamus-pituitary-interrenal axis, leading to alterations in blood hormone levels. This activation may lead to changes in metabolism, including a rise in lactic acid and glucose levels. Therefore, blood glucose and lactic acid are the prevalent indicators of response stress in fish. Several investigations have shown that the levels of blood glucose and lactic acid in anesthetized fish were considerably elevated compared to non-anesthetized fish. In contrast, some investigations have found that the use of anesthesia and handling with essential oil did not alter the levels of lactic acid and glucose in the blood. This might be because different species react differently to anesthetics. The level of glucose in the fish anesthetised with *Cinnamomum camphora* essential oil was lower than that of the fish anesthetised with MS-222 and linalool in this study. Elevated glucose levels are considered helpful for fish when they face stress. After 24 h of resuscitation, the glucose concentration of the fish anesthetised with linalool was higher than that of the fish anesthetised with MS-222 and *Cinnamomum camphora* essential oil, indicating that anesthetic pressure was still present.

5. Oxidative Stress

Figure 6A:
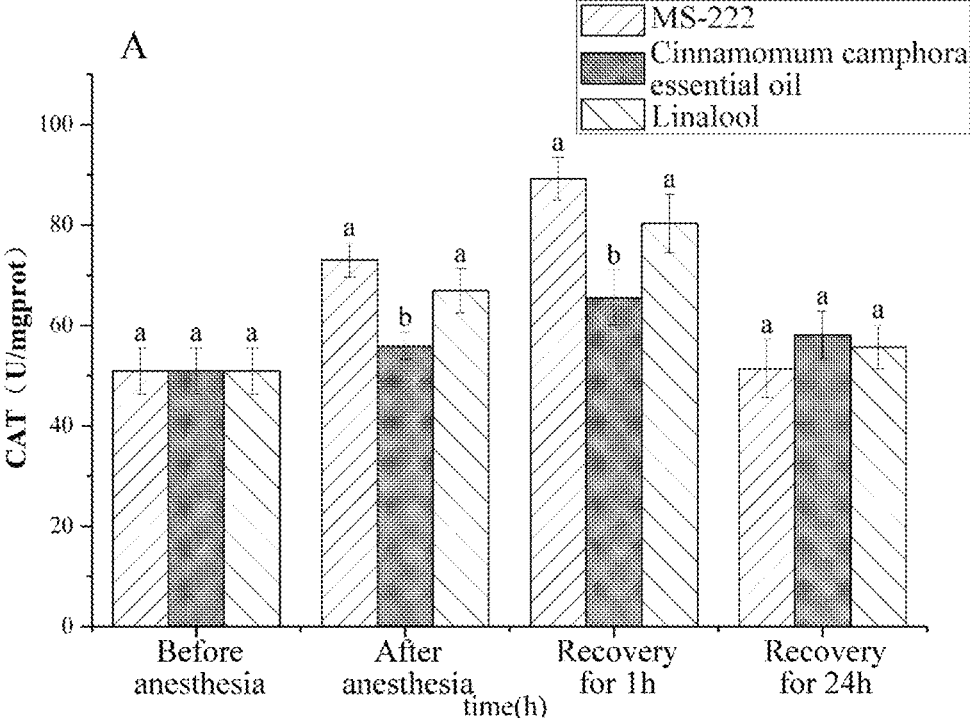
FIGS. 6A-6C show effects of MS-222, *Cinnamomum camphora* essential oil and linalool anesthesia on oxidative stress of the spotted seabass; wherein A, catalase (CAT); B, glutathione peroxidase (GSH-Px); and C, superoxide dismutase (SOD)
Figure 6B:
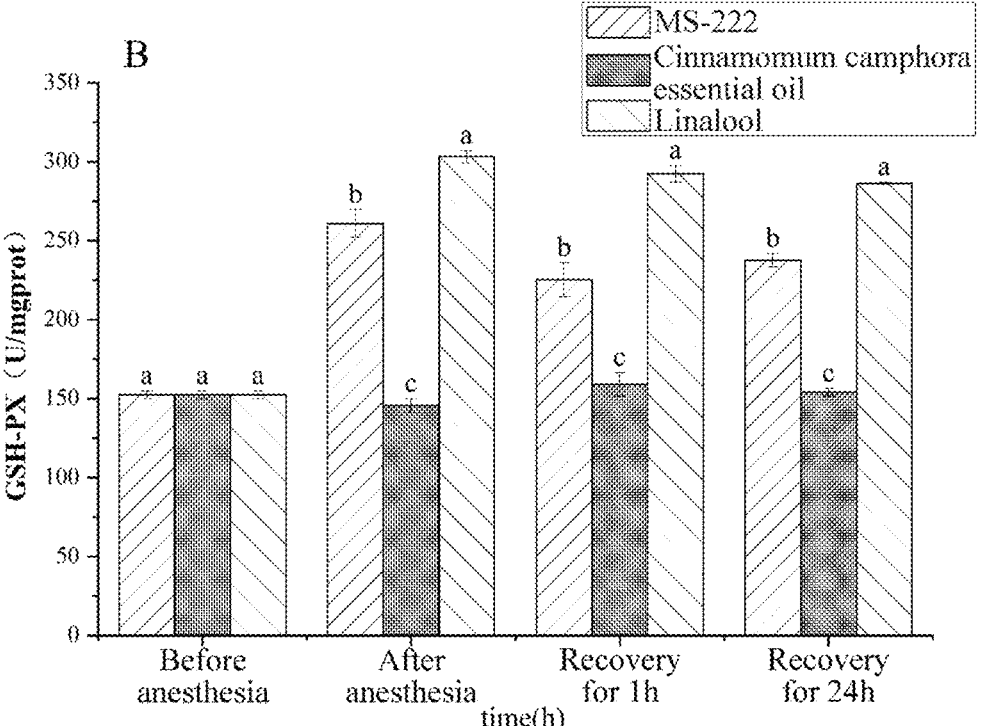
Figure 6C:
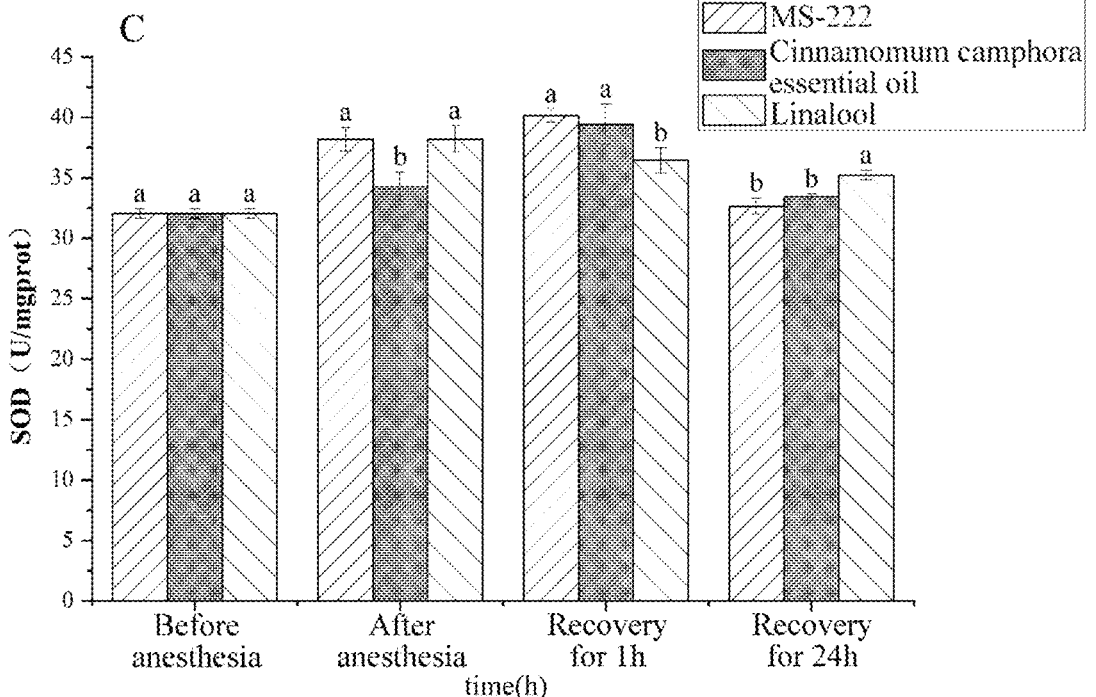

Antioxidant enzymes play a crucial role in response to oxidative stress. SOD, CAT and GSH-Px are crucial enzymes in the antioxidant defence systems and serve as the initial defensive mechanism of cells against oxidative stress. The SOD preferentially removes superoxide anion radicals to generate $H_2O_2$. Then the CAT and GSH-Px will break down the $H_2O_2$ into water After anesthesia, the SOD, CAT and GSH-Px activities of spotted seabass in the MS-222, *Cinnamomum camphora* essential oil and linalool groups showed an increasing trend. Among them, spotted seabass in the *Cinnamomum camphora* essential oil group had the smallest amount of change, with 6.90%, 9.77% and 4.53% changes in SOD, CAT and GSH-Px, respectively. The positive effects of anesthetics on the antioxidant system have been previously highlighted in the definition of an ideal anesthetic. Anesthetics can alter oxygenation in tissues and have antioxidant effects at appropriate concentrations. For example, chamomile oil and clove oil enhanced the antioxidant capacity of fish when anesthetized. In contrast, the *Cinnamomum camphora* essential oil had some antioxidant capacity and reduced anesthetic stress in spotted seabass, resulting in minimal oxidative stress. In contrast, the SOD, CAT and GSH-Px activities of spotted seabass in the MS-222 and linalool groups varied considerably. Although the SOD and CAT activities of spotted seabass in the MS-222 and *Cinnamomum camphora* essential oil groups recovered to the initial values after 24 h of recovery, only the spotted seabass in the *Cinnamomum camphora* essential oil group returned the initial levels of the GSH-Px activities. However, the SOD and GSH-Px activities of spotted seabass in the linalool group were still higher than the initial levels, indicating that oxidative stress still existed (FIGS. 6A-6C).

6. Immune Response

Figure 7A:
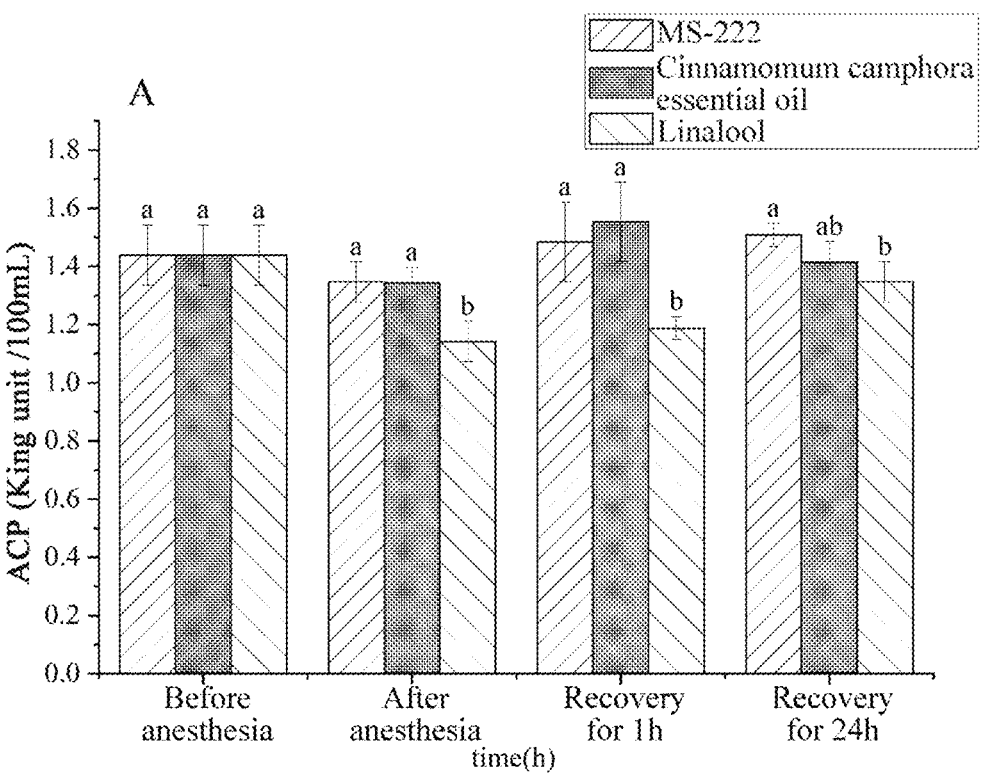
FIGS. 7A-7C show effects of MS-222, *Cinnamomum camphora* essential oil and linalool anesthesia on immune response of the spotted seabass; wherein A, acid phosphatase (ACP); B, immunoglobulin M (IgM); and C, lysozyme (LZM).
Figure 7B:
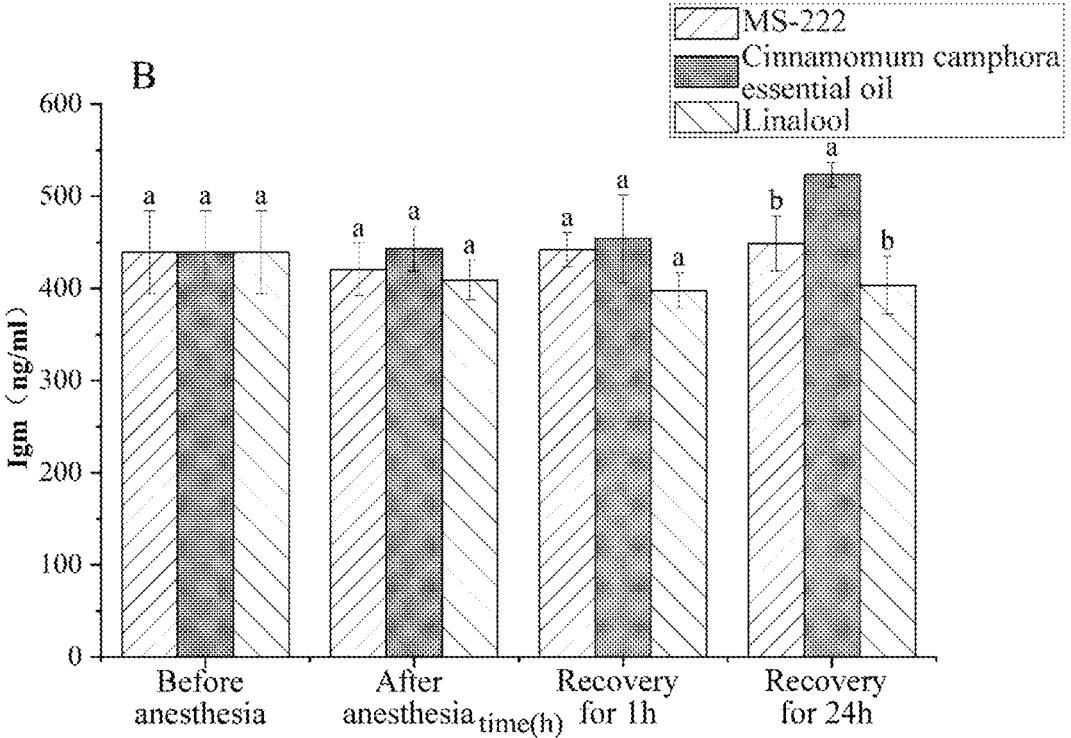
Figure 7C:
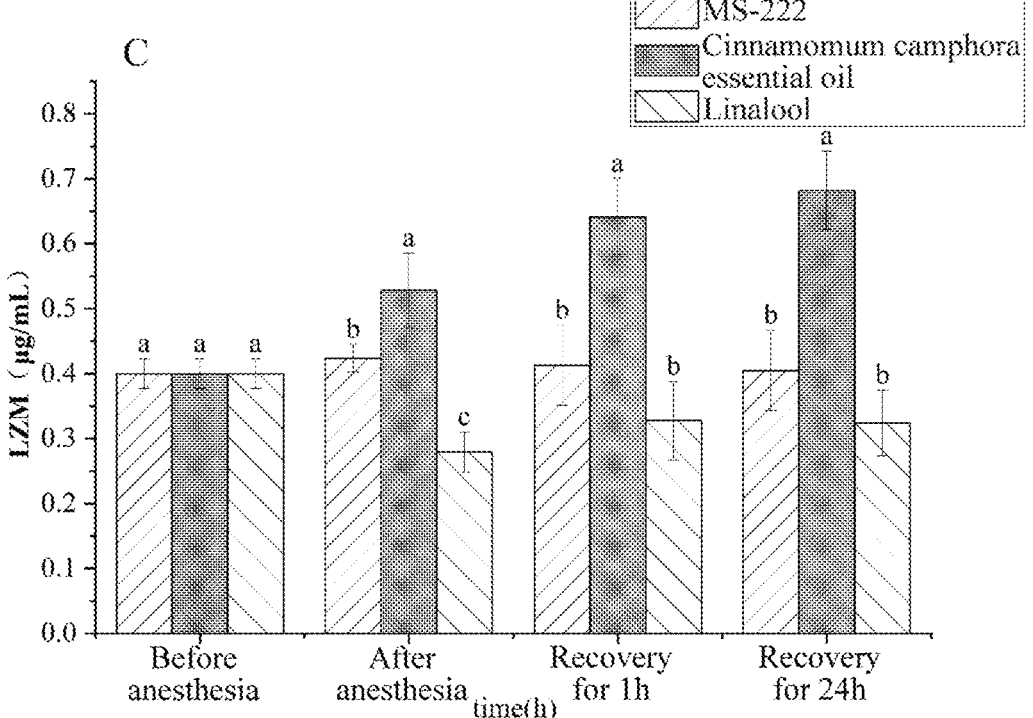

Both ACP and LZM activities in fish anesthetised linalool with were higher (P<0.05) than those in fish anesthetised with MS-222 and *Cinnamomum camphora* essential oil. In addition, the LZM activity of sptted seabass anesthetised with *Cinnamomum camphora* essential oil was significantly higher than that of sptted seabass anesthetised with MS-222 (P<0.05). After 24 h of recovery, the activities of AKP and IgM were restored in all treatment groups, while the LZM activity of spotted seabass anesthetised with *Cinnamomum camphora* oil was higher than that of spotted seabass anesthetised with MS-222 and linalool (P<0.05) (FIGS. 7A-7C).

The fish immune system contains a wide range of immunological components and enzymes, including total IgM, LZM, and AKP levels, which were assessed in the current study. AKP is thought to be a part of the fish immune system and is a crucial signal of stress. The AKP activity is modest under normal conditions and elevated levels of ALP activity in the serum indicate tissue or organ damage. According to the present results, the AKP activities increased when fish were exposed to MS-222, *Cinnamomum camphora* essential oil and linalool. Similar to the results of other authors, the use of MS-222 caused an elevation in the serum AKP activities in *L. maculatus*. The liver damage might be attributed to drug metabolism resulting from extended exposure to the anesthetic. Another study discovered that linalool, when exposed to for an extended period, can lead to increased AKP activity compared to citronellal and eugenol.

In the present study, IgM concentrations decreased in fish anesthetised with MS-222 and linalool. Soltanian et al. found that exposure to 2-phenoxyethanol caused a considerable drop in IgM levels in the skin mucus of *Oncorhynchus mykiss*. However, *Cinnamomum camphora* oil did not have significant effects on the IgM levels after anesthesia. Several investigations have indicated that stress promotes variations in LZM and IgM levels in fish serum. Therefore, it's speculated that the reduced IgM concentration may be associated with immunoreactions induced by anesthesia.

LZM activities decreased in the fish anesthetised with MS-222 and increased in the fish anesthetised with *Cinnamomum camphora* essential oil and linalool. After 24 h of resuscitation, LZM activities in three groups recovered to the initial levels. This result aligns with the discoveries made by Soltanian et al. in the serum of *O. mykiss*. Studies have shown that anesthetics have an inhibitory fish immunity, and this impact is influenced by the specific type and dosage of the anesthetic used. However, LZM activity did not decrease in the fish with *Cinnamomum camphora* essential oil and linalool, and an increase in LZM activity might increase the level of neutrophilia after exposure to *Cinnamomum camphora* essential oil and linalool.

The plant essential oil anesthesia method of spotted seabass in the present disclosure can effectively reduce oxidative stress and immunosuppression in spotted seabass during anesthesia, effectively slow down anesthesia-induced injury to gills, and maintain homeostasis at hematological levels. While obtaining good and safe anesthesia effect, compared with the expensive MS-222, the price of the *Cinnamomum camphora* essential oil is only 1/10 thereof, which effectively reduces the anesthesia cost, and can be applied to the process of vaccination, blood sampling, weighing and transporting of the live fish, so as to obtain a higher economic benefit.

The above embodiments are merely illustrative and not intended to limit the scope of the disclosure. It should be understood that any modifications and replacements made by those skilled in the art without departing from the spirit of the disclosure should fall within the scope of the disclosure defined by the appended claims.

What is claimed is:

1. A method of anesthetizing a spotted seabass with a *Cinnamomum camphora* essential oil, consisting essentially of:

a) acclimating the spotted seabass in a water tank for 24 hours before performing anesthesia, wherein the water quality parameters are maintained within following ranges: dissolved oxygen at 6.0 mg/L, temperature at $22 \pm 1°$ C., salinity of 16%, and pH at 7.5-8.0;

b) discharging the metabolic wastes of the spotted seabass during an acclimatization period;

c) emulsifying and dissolving *Cinnamomum camphora* essential oil, ethanol, and Polysorbate 80 to obtain an emulsified *Cinnamomum camphora* essential oil;

d) adding the emulsified *Cinnamomum camphora* essential oil into seven different aquariums at concentrations of 10 mg/l, 20 mg/l, 30 mg/l, 50 mg/l, 100 mg/l, 150 mg/l, and 200 mg/l, respectively, e) transferring the spotted seabass to the seven different aquariums with the emulsified *Cinnamomum camphora* essential oils of the different concentrations, respectively;

f) recording the concentrations of the *Cinnamomum camphora* essential oils in the seven different aquariums of spotted seabass and the anesthesia time of the spotted seabass;

g) extracting the spotted seabasses once deep anesthesia is achieved; and h) recording the resuscitation time of the spotted seabasses when the spotted seabasses restore their swimming behavior.

* * * * *